(12) United States Patent
Yang

(10) Patent No.: US 8,114,644 B1
(45) Date of Patent: Feb. 14, 2012

(54) PROCESS FOR PRODUCING SHORT CHAIN ALCOHOLS FROM LIGNIN

(75) Inventor: Fangxiao Fx Yang, Butte, MT (US)

(73) Assignee: Resodyn Corporation, Butte, MT (US)

( * ) Notice: Subject to any disclaimer, the term of this patent is extended or adjusted under 35 U.S.C. 154(b) by 365 days.

(21) Appl. No.: 12/357,652

(22) Filed: Jan. 22, 2009

Related U.S. Application Data

(60) Provisional application No. 61/022,746, filed on Jan. 22, 2008.

(51) Int. Cl.
*C12P 7/16* (2006.01)
*C12N 1/20* (2006.01)

(52) U.S. Cl. ......... 435/160; 435/162; 435/155; 435/132

(58) Field of Classification Search .................. 435/160, 435/162, 155, 132
See application file for complete search history.

(56) References Cited

U.S. PATENT DOCUMENTS

| | | | | |
|---|---|---|---|---|
| 5,063,156 | A * | 11/1991 | Glassner et al. | 435/151 |
| 5,192,673 | A * | 3/1993 | Jain et al. | 435/160 |
| 5,357,636 | A * | 10/1994 | Dresdner et al. | 2/161.7 |
| 6,555,350 | B2 * | 4/2003 | Ahring et al. | 435/162 |

\* cited by examiner

*Primary Examiner* — Chin-Min Kim
(74) *Attorney, Agent, or Firm* — Paul and Paul

(57) ABSTRACT

Biomass is converted to short chain alcohols such as butanol by a process which comprises (1) reacting biomass with an oxidizing agent to produce unoxidized aromatic and/or phenolic compounds and $C_{1-6}$ linear and branched, saturated and unsaturated carboxylic acids; (2) separating the unoxidized aromatic and/or phenolic compounds from the $C_{1-6}$ carboxylic acids; (3) anaerobically fermenting the $C_{1-6}$ carboxylic acids in the presence of an anaerobic bacterium in its solventogenesis phase to produce a solvent comprised of butanol and non-fermentable carboxylic acids. The products of the process can be used as fuel and/or fuel additives.

16 Claims, 3 Drawing Sheets

PROCESS FOR PRODUCING SHORT CHAIN ALCOHOLS FROM LIGNIN

CROSS-REFERENCE TO RELATED APPLICATIONS

This Application claims the benefit of copending Provisional Application Ser. No. 61/022,746, filed on Jan. 22, 2008, the entire contents of which are incorporated herein by reference.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

Because more and more corn grain is diverted to ethanol production from use as a food, food shortage concerns have arisen. However, ethanol made from cellulosic materials such as stems, leaves, stalks and trunks of plants instead of corn grain would ameliorate concerns over the food supply. Furthermore, any cellulosic biomass for ethanol production can be converted to butanol as well for auto fuel. Butanol is in several ways more similar to gasoline than is ethanol. Butanol can, therefore, be used by itself as fuel in internal combustion engines and has been demonstrated to work in some vehicles designed for use with gasoline without any modification. Butanol can be produced from biomass as well as fossil fuels. Butanol produced via fermentation is called biobutanol to reflect its origin, although it has the same chemical properties as butanol produced from petroleum. Butanol is currently an industrial commodity and mainly manufactured from petroleum, with a 370 million gallons per year market with a selling price of about $3.75 per gallon. Indeed, butanol has higher energy content (110,000 Btu per gallon for butanol as compared to 84,000 Btu per gallon for ethanol). Gasoline contains about 115,000 Btu's per gallon. Butanol is six times less "evaporative" than ethanol and 13.5 times less evaporative than gasoline, making it safer to use as an oxygenate in Arizona, California and other "hot" states, thereby eliminating the need for very special blends during the summer and winter months. There has been little to no effort to promote butanol as an alternate fuel because of historically low yields and low concentrations of butanol being produced through Acetone-Butanol-Ethanol (ABE) fermentation compared to those of ethanol.

(2) Description of Related Art, Including Information Disclosed Under 37 C.F.R. Sections 1.97 and 1.98.

Acetone/butanol/ethanol (ABE) is an anaerobic fermentation process capable of producing commodity chemicals, such as butanol and acetone, from biomass. It is known in the art that *Clostridium acetobutylicum* can be used as the bacterium in ABE fermentation. For example, U.S. Pat. No. 5,192,673, the entire contents of which are incorporated herein by reference, describes an improved fermentation process for producing high levels of butanol using a mutant strain of *Clostridium acetobutylicum* designated *Clostridium acetobutylicum* ATCC 55025.

After cellulose, lignin is the most abundant biomass found in nature. Lignin fills the spaces in the plant cell wall between cellulose, hemicellulose and pectin components. The paper industry produces a great deal of lignin in the form of a substance known as "black liquor," from the pulping process which essentially delignifies wood chips to form paper-making fibers. Black liquor is an aqueous solution of lignin residues, hemicellulose, and inorganic chemicals used in the pulping process wherein wood is delignified into wood fibers, lignin and hemicellulose.

Wheat straw, which is a waste product in most agricultural operations, is a type of cellulose that is relatively easy to delignify. Over 126 million metric tons of wheat straw are produced in the United States every year. For this reason, wheat straw has been targeted as feedstock to convert to a biobutanol fuel.

BRIEF SUMMARY OF THE INVENTION

In its broadest aspect, the present invention pertains to a process for converting the lignin in biomass to short chain, linear and branched, saturated and unsaturated organic acids and sequentially to short chain, linear and branched, saturated and unsaturated alcohols such as butanol via fermentation. In another aspect, the present invention pertains to a process for the production of fuel and fuel additives from biomass comprising the steps of: (1) oxidizing biomass to form unoxidized aromatic and/or phenolic compounds and $C_{1-6}$ linear and branched, saturated and unsaturated carboxylic acids; (2) separating the unoxidized aromatic and/or phenolic compounds from the $C_{1-6}$ carboxylic acids; (3) anaerobically fermenting the $C_{1-6}$ carboxylic acids in the presence of an anaerobic bacterium in its solventogenesis phase to produce a solvent comprised of short chain, linear and branched, saturated and unsaturated alcohols such as butanol and non-fermentable acids. The process according to the invention is optionally comprised of the step of esterifying any non-fermentable acids produced in step (3) with alcohols produced in step (3). Another aspect of the present invention relates to a process for the production of fuel and fuel additives from lignin.

The esters formed in the optional step of the process according to the invention can be used as oxygenating additives for fuels. More specifically, during lignin oxidation to carboxylic acids, intermediate products such as phenol and/or poly-phenols are produced. These products can be used without separating them from the reaction mixture as oxygenated fuel additives to vegetable oil, animal fat and recycled grease for diesel engine and boiler fuels. With the addition of lignin oxidation intermediate products, straight vegetable oil (SVO) and/or grease can perform in internal combustion engines or in boilers as petroleum diesel without chemical modification. These SVO fuel mixtures have similar viscosities, cloud points and fuel consumption rates as conventional petroleum diesel fuel.

DETAILED DESCRIPTION OF THE INVENTION

The oxidation step of the process according to the invention is a deep (extensive) oxidation (DOX) of lignin whereby lignin from biomass hydrolysis is converted to linear and branched, saturated and unsaturated $C_{1-6}$ carboxylic acids. The oxidation can be carried out in supercritical water, supercritical carbon dioxide, or heated alkaline solution as reaction medium. The oxidizing agent can be any oxidizing agent that converts the biomass to $C_{1-6}$ carboxylic acids. Preferably, the oxidizing agent is molecular oxygen, ozone, organic peroxides or hydrogen peroxide.

Figure 1:
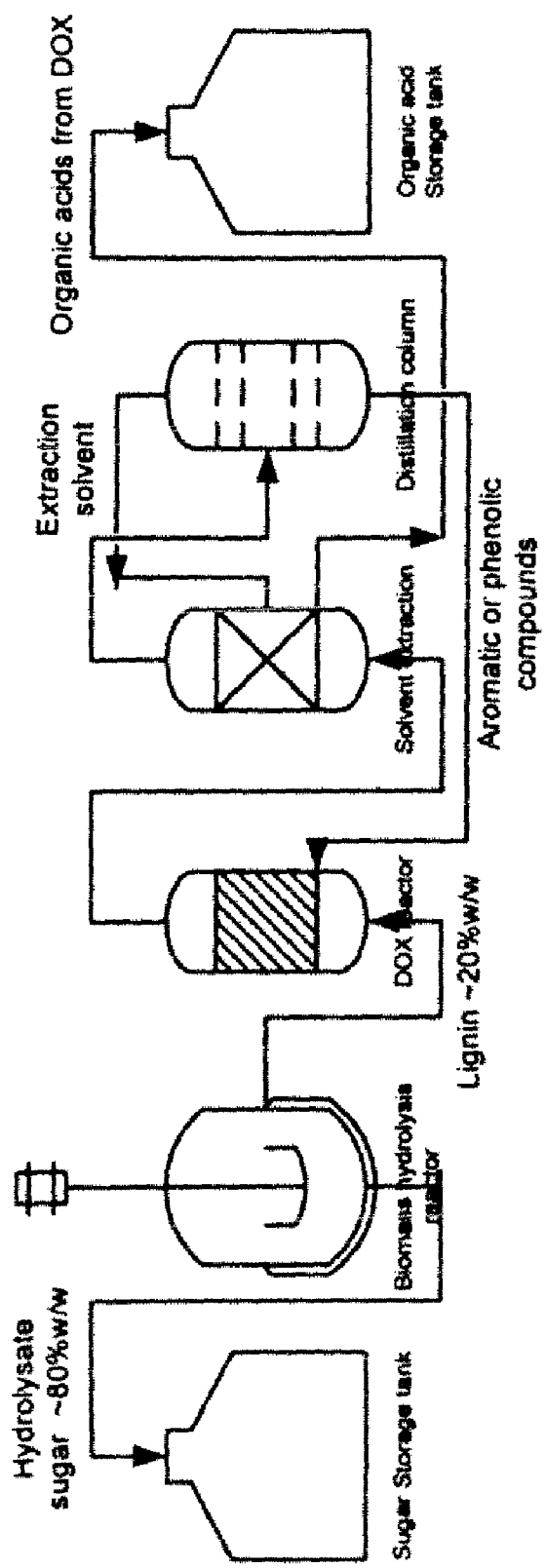
FIG. 1 is a schematic process flow diagram illustrating one embodiment of the first step in the process of the present invention which deals with lignin oxidization to $C_{1-6}$ carboxylic acids and their recovery and separation. This embodiment of the process includes four unit operations; biomass hydrolysis, lignin deep oxidation, solvent extraction and distillation.
Figure 2:
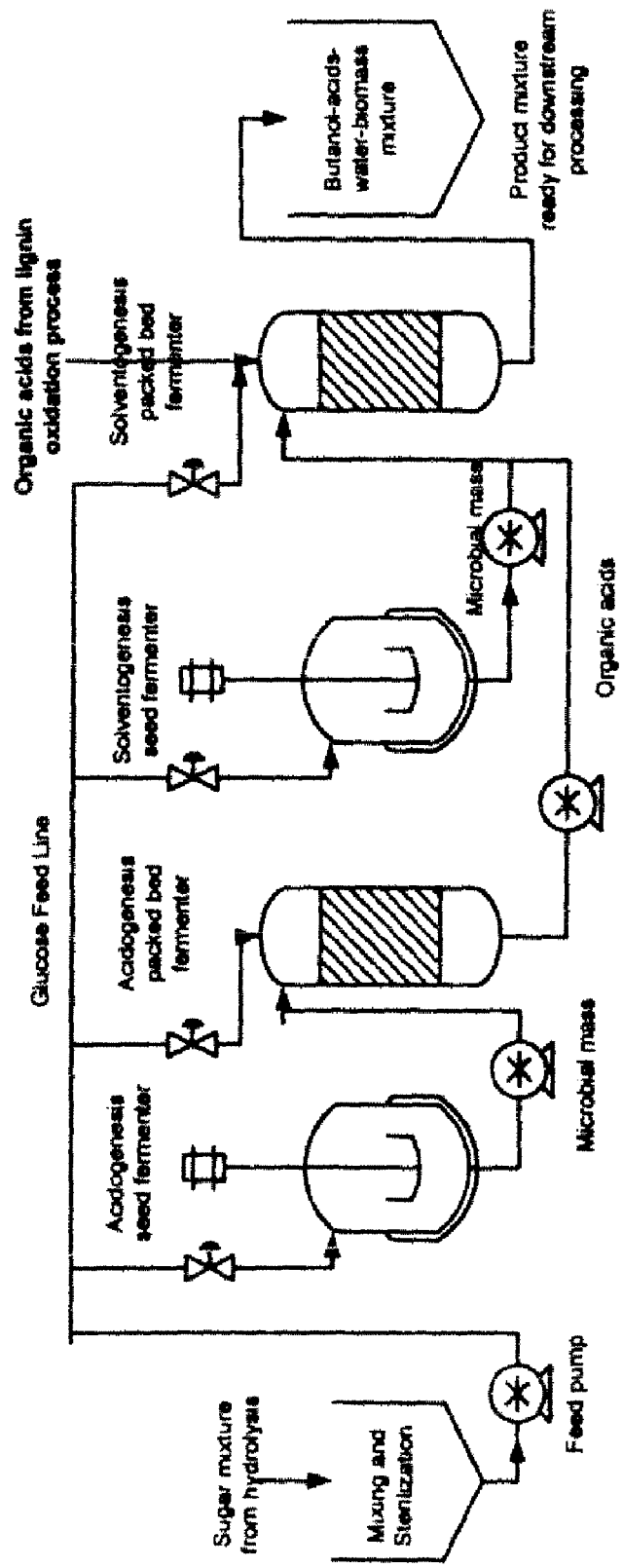
FIG. 2 is a schematic process flow diagram illustrating one embodiment of the second step in the process of the present invention. Organic acids produced in step 1 of the process are converted to the corresponding alcohols, including butanol, by fermentation in the presence of an anaerobic bacterium in its solventogenesis phase. This embodiment of the process includes acidogenesis seed production, acidogenesis fermentation, solventogenesis seed production and solventogenesis fermentation.

In a preferred embodiment of the process according to the invention, the DOX process can be carried out in at least four unit operations which comprise: (1) a Biomass Hydrolysis Reactor where lignocellulose materials such as wheat straw are hydrolyzed for sugar release and lignin is recovered from the operation; (2) a Lignin Deep Oxidation (DOX) Reactor in which lignin is converted organic acids through a catalytic process; (3) a Solvent Extraction Vessel where unconverted aromatic compounds from lignin fragments are extracted into an organic extraction solvent such as hexane and remaining organic acids are pumped to a solventogenesis fermenter as detailed in FIGS. 1) and (2); (4) a Distillation Column where the extraction solvent is separated from unconverted aromatic compounds. The solvent is recycled back to the extractor, and the recovered unconverted compounds are fed back to the DOX reactor. This extract is fed to a continuous enzyme packed bed fermentation reactor which provides sufficient residence time to achieve high conversion, preferably ≧99.995%, of organic acids, especially short chain carboxylic acids such as butyric acid, acetic acid or propionic acid.

Preferably, the fermentation step includes six unit operations which comprise: (1) a Feed Mixer where carbohydrate or sugar produced from the previous hydrolysis process is sterilized and then pumped to fermentation reactors; (2) an Acidogenesis Seed Fermenter in which microbial seed for acidogenesis is grown to reach a certain cell density; (3) an Acidogenesis Packed Bed Fermenter in which sterilized and pretreated straw is packed in a column and the microbial seed from upstream is fed to the bed in which the microbial cells are immobilized on the straw by adsorption and convert sugar from hydrolysis to $C_{1-6}$ carboxylic acids such as butyric acid and other organic acids; (4) a Solventogenesis Seed Fermenter in which microbial seed for solventogenesis are grown to reach a certain cell density; (5) a Solventogenesis Packed Bed Fermenter in which sterilized and pretreated straw are packed in a column and the microbial seed from upstream is fed to the bed in which cells are immobilized on the straw by adsorption. (6) After cell density is stabilized, the packed bed becomes the fermenter to convert acids from acidogenesis fermentation into $C_{1-6}$ alcohols such as butanol, ethanol and other types of compounds such as ketones for example acetone. Acids obtained from DOX process are added into this fermenter as supplement feedstock.

The microorganism that can be used in the process according to the invention is any bacterium that can convert carboxylic acids into alcohols such as, preferably, *Clostridium acetobutylicum* ATCC 55025 and ATCC 39236.

Preferably, in a step subsequent to step (3) of the process according to the invention, the short chain organic acids such as acetic and butyric acids from the fermentation step can be converted to their corresponding alkyl esters, for example, butyl acetate, for use as butanol fuel additives and oxygenating agents. The fruity-smelling esters also serve as deodorizing agents for the fuel. Since the reaction is an esterification reaction, water, which is one of the products of the fermentation, can be removed from the stream before feeding to esterification reactors. Solvent extraction and other methods of removing water from the butanol stream after ABE fermentation may be employed for this purpose. At this point, the products from fermentation can be separated from the culturing media, i.e., without microbial cell or cell debris, and other nutrition residual. Since the mixture contains primarily alcohols, ketones and organic acids, the major enzymatic reactions occur between alcohols and organic acids. The principal products of the esterification reaction are esters and water. Although water can be removed from the product stream, the produced esters remain in the product mixture as fuel additives.

The esterification (ET) reactor can be a packed bed column in which the medium is a solid acid such as Dowex 2030, or an immobilized lipase enzyme. A solution of butanol, ethanol and/or other short chain organic acids can be pumped through the bed and the organic acids converted into ethyl or butyl esters with the production of water. When the esterification is carried in the presence of an enzyme catalyst, the enzyme reactor can be a packed bed filled with immobilized lipase enzymes, preferably in the form of a column having a height to diameter ratio of 1:100, preferably 5:12. For relative strong solid acid catalysts, an agitated vessel can be used as the reactor. For solid acid reactor, the operation temperature can be as high as 65° C. to promote reaction rate, while the enzyme reactor needs only room temperature to have reasonable reaction rate. The effluent from ET reactor can be fed to a molecular sieve column (packed bed) where water can be removed by adsorption. The dried stream can then be fed to a distillation column where other organic liquids are separated from the butanol-ester mixture. The esters do not have to be separated from butanol and can remain in the solvent mixture as oxygenators for butanol fuel. The water-free butanol-fuel mixture can be readily pumped to a transportation truck.

Enzymes that can be used in the esterification reaction include, but are not limited to, Lipase M® (Amano Pharmaceutical Co., Ltd., from *Mucor javanicus*), Palatase M® (Novozyme A/S, from *Mucor miehei*), Lipase F® (Amano Pharmaceutical Co., Ltd., from *Rhizopus* sp.), Talipase® (Tanabe Seiyaku Co., Ltd., from *Rhizopus delemar*), Neurase F® (Amano Pharmaceutical Co., Ltd., from *Rhizopus niveus*), Lipase MY® (Meito Sangyo Co., Ltd., from *Candida cylindracea*), Lipase A® (Amano Pharmaceutical Co., Ltd., from *Aspergillus niger*), Lipase Au® (Shin Nihon Chemical Co., Ltd., from *Arthrobacter ureafaciens*), Lipase P® (Amano Pharmaceutical Co., Ltd., from *Pseudomonas* sp.), and Lipase SP® (Toyo Jozo Co., Ltd., from *Chromobacterium viscosum*). Preferred commercially available enzyme preparations derived from animals include pancreatic Lipase 250® (Kyowa Solzyme Co., Ltd., from pig pancreas), Lipase 400® (Kyowa Hi Foods Co., Ltd., from sheep and goat pharynx), and Lipase 600® (Kyowa Hi Foods Co., Ltd., from cow pharynx). The activity of the enzyme lipase, as a catalyst, is typically expressed in international unit (IU). One international unit as used herein is defined as the potency of the enzyme activity which produces 1 micromole of ethyl butyrate in 1 minute, under the assay conditions described in the following method for determining ester-synthesizing activity.

Ester-synthesizing activity can be determined by measuring the amount of ester, such as ethyl butyrate produced when ethanol and butyric acid are the substrates. The substrate solution is prepared by adding 0.5 percent by weight or 5 percent by weight ethanol and 2.6 percent by weight butyric acid to a 0.1 M phosphate buffer solution (pH 6). The pH is adjusted to 6 using sodium hydroxide. To 1.9 milliliters (ml) of the substrate solution is added 0.5 grams of immobilized lipase. The mixture is then placed on a rotator running at 60 revolutions per minute (rpm) at 30° C. for 25 minutes, and 1 ml of acetone is added to stop the reaction. Next, 2.0 ml of aqueous ethyl ether containing 50 micromolar (µM) ethyl caproate as the internal standard is added and mixed, and the mixture is allowed to stand for 10 minutes. The upper layer liquid phase is then subjected to gas chromatography to determine the amount of ethyl butyrate produced. Also, to the same substrate solution containing 1 ml of acetone, the enzyme particles are added and the resulting mixture is used as the blank sample. The enzyme activity is expressed, defining the amount of enzyme which produces 1 µmol of ethyl butyrate in 1 minute under the conditions described above (0.5 percent ethanol concentration in the reaction system) as one international unit.

The ET reactor can be operated at a temperature of from 10 to 100° C., preferably from 20 to 35° C. for an enzyme packed bed, and from 10 to 150° C., preferably from 40 to 65° C. for a solid acid packed bed or a stirred tank reactor. For an enzyme catalyzed process, a packed bed is most preferred because the immobilized enzyme particles are very fragile, and any agitation leads to particle fracturing. For enzymatic ET reactions, operation at room temperature saves operational costs and prolongs enzyme stability. Since completely dehydrated enzymes are not active, a small amount of water is associated with the enzyme and its support from the manufacturer. This amount of water is not sufficient for optimal enzyme activity. As the conversion of acid to ester progresses, water is built up as a product of the esterification reaction. This water is absorbed by the enzyme first, then by ethanol and the enzyme support. A dynamic equilibrium exists between the ethanol solution phase, the enzyme and its support. If the enzyme becomes saturated with water, its catalytic activity decreases and is eventually deactivated because the catalyst conformation is changed. The enzyme also loses its activity after a certain number of turnovers, which is the number of times the catalyst converts reactant molecules to the corresponding product. Typically, the time to reach this point is much longer than the point of enzyme lost activity due to water saturation. However, in this process, excess ethanol and acetone in the feed stream mixture prevent water accumulation on enzyme particles. The symptom of enzyme losing its activity is a decreasing conversion rate in the effluent stream. This can be monitored using an automated organic acid titration apparatus wherein the endpoint of the titration is shown by an indicator color change detected by means of a spectrophotometer. A typical residence time is between 15 minutes to 25 minutes, depending on the organic acid content of the feed. Typically, the decrease in conversion is observed after 70 to 100 days operation if no water accumulated with enzymes.

The water produced during the ET process must be removed to prevent deactivation of the catalysts because water tends to accumulate near the catalyst particles, which can cause catalyst deactivation. The effluent from the column is continually monitored for the presence of organic acids by any means that detects acids—typically by an automated titrimetric method wherein the endpoint of the titration is indicated by a color change in an indicator detected spectrophotometrically. A predetermined acid concentration is used as a feedback control of the feeding flow rate to the ET reactor. The ET reactor can be an agitated tank, a fluidized bed or a sonic mixed tank in which water is continually removed, preferably as an ethanol-water azeotrope.

The solid acid catalyst reactor (either a packed bed or a stirred tank) is preferably operated at 65° C. and 100 psig. Due to their physical robust nature, the reaction mixture with catalyst beads can be agitated and the operation can be conducted at elevated temperature. The catalytic esterification process can be a set of reactors. In this process, a solid acid catalytic reactor is used in the first part to convert most of the organic acid, and in the second part, an enzyme packed bed is used to finish the residual of the organic acid. Between the solid acid reactor and the enzyme, a condenser is required to cool down the effluent from the former reactor and keep the feed in liquid form after it is de-pressurized. For larger operations, scaling up of the reaction is done in a straightforward manner for a packed bed by applying the same residence time requirement for the volume of fluid to be processed, as long as the geometric constraint of the reactor aspect ratio remaining between 5:1 and 12:1 H/D is observed.

Figure 3:
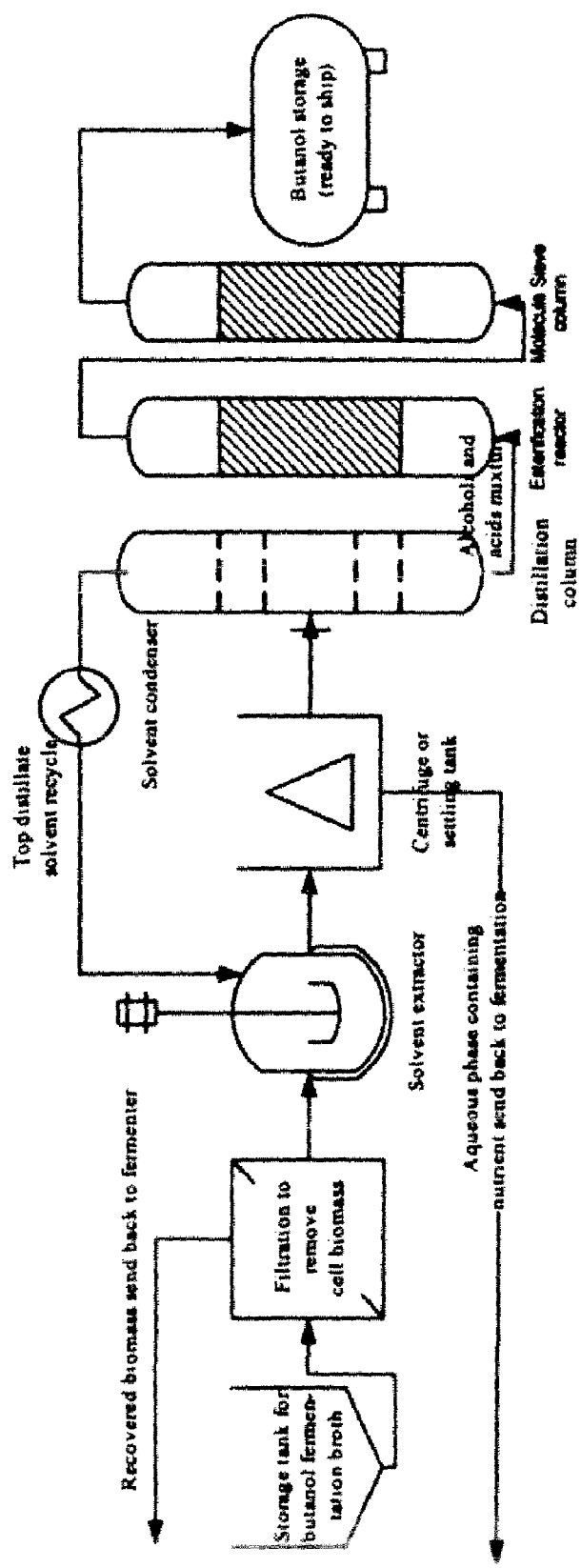
FIG. 3 is a schematic process flow diagram illustrating one embodiment of the third step in the process of the present invention. Butanol and other organic compounds formed in step 2 are extracted from the fermentation broth. The unconverted organic acids are converted to esters which function as fuel additives. This embodiment of the process is comprised of five unit operations which include filtration, solvent extraction, centrifugation, distillation and esterification.

FIG. 3 illustrates a preferred process for butanol separation and the treatment of the final product mixture. The process includes five unit operations which comprise: (1) a Filtration Vessel wherein the fermentation cell biomass is separated from the product solution; (2) a Solvent Extractor wherein organic materials including butanol and organic acids are extracted into an organic solvent phase and thereby separated from water; (3) a Settling Tank (ST) or a Centrifuge wherein the aqueous phase is separated from the organic phase (organic solvent plus butanol mixture); (4) a Distillation Column (DC) wherein the extraction solvent is separated from the butanol product mixture and recycled back to the solvent extractor; (5) an Esterification Reactor (ET) where the organic phase containing butanol and the organic acids are introduced and organic acids are reacted with ethanol and/or butanol to form esters. The catalysts for this step can be solid acids or immobilized enzymes or a combination of the two. The reactor can be a packed bed, a continuous stirred tank, or a sonically agitated tank. In an optional sixth step, water produced during the esterification process is removed from the organic mixture by means of a molecular sieve (MS) column. The molecular sieve can be regenerated by any means known those of ordinary skill in the art.

The following six examples describe how the invention may be carried out. They are meant to illustrate but not to limit the invention.

EXAMPLES

Alkaline oxidation: An aqueous solution having a lignin concentration of from 20 to 80 g/L (from straw hydrolysis) at a temperature range of 130 to 200° C. is contacted with an oxygen partial pressure in the range of 3 to 10 bar, and a 2 to 10 N NaOH solution. The reaction products are extracted from the aqueous medium by butanol or pentanol. The concentration of produced organic acids is determined through a titration method. The remaining lignin concentration is determined through chromatography methods (GC or HPLC).

Unconverted aromatic compounds separation: The unconverted aromatic and phenolic compounds are extracted from the oxidation mixture with toluene or other solvents. These aromatic compounds are then recovered through a distillation process and fed back to the oxidation step. The extraction solvent is then recycled back to extraction vessel.

Supercritical water oxidation with peroxide as oxidant: A solution containing 20 to 80 g/L lignin is heated and pressurized to the water supercritical condition. Various hydrogen peroxide concentrations from 3.5 to 15 g/L are used. The reaction time is varied from 5 seconds to 5 minutes. The products of the oxidation are separated and analyzed as described previously.

Lignin oxidation in supercritical $CO_2$ with peroxide: Hydrogen peroxide ($H_2O_2$) is used first to determine to what extent the oxidation can go with this oxidant. $CO_2$ is heated to 31° C. and pressurized to 73 atm. A solution containing 20 to 80 g/L lignin and a stream of $H_2O_2$ are pumped into the system. The parameters determining the product composition to be investigated includes treatment duration, temperature, pressure and the concentration of hydrogen peroxide.

Lignin oxidation in supercritical $CO_2$ with ozone: $CO_2$ are heated to 31° C. and pressurized to 73 atm and a solution containing 20 to 80 g/L lignin and a stream of ozone are pumped into the system. The final reaction pressure and temperature, ozone concentration in SFC $CO_2$ are varied to optimize the acid formation and minimize the energy cost.

Supercritical water oxidation with ozone as oxidant: A solution having a lignin concentration at 20 to 80 g/L is added to DI water and an appropriate amount of oxidant is added. The conditions are similar to those for ozone described above. The parameters to be investigated are dosage of ozone added, water temperature and pressure and lignin treatment duration.

The invention claimed is:

1. A process for the production of fuel and fuel additives comprising the steps of: (1) reacting biomass with an oxidizing agent to produce unoxidized aromatic and/or phenolic compounds and $C_{1-6}$ linear and branched, saturated and unsaturated carboxylic acids; (2) separating the unoxidized aromatic and/or phenolic compounds from the $C_{1-6}$ carboxylic acids; (3) anaerobically fermenting the $C_{1-6}$ carboxylic acids in the presence of an anaerobic bacterium in its solventogenesis phase to produce a solvent comprised of short chain, linear and branched, saturated and unsaturated alcohols and non-fermentable carboxylic acids.

2. The process of claim 1 wherein step (1) is carried in a solvent selected from the group consisting of supercritical water, supercritical carbon dioxide, and an aqueous alkaline solution.

3. The process of claim 1 wherein the oxidizing agent in step (1) is selected from the group consisting of molecular oxygen, ozone, organic peroxides and hydrogen peroxide.

4. The process of claim 1 wherein the anaerobic bacterium is selected from the group consisting of *Clostridium acetobutylicum* ATCC 55025 and ATCC 39236.

5. The process of claim 1 further comprising the step of forming an ester by reacting the non-fermentable acids and alcohols produced in step (3).

6. The process of claim 5 wherein the ester is butyl acetate.

7. The process of claim 1 wherein the alcohol formed in step (3) is butanol.

8. The process of claim 1 wherein the acid formed in step (3) is acetic acid.

9. The process of claim 1 wherein the biomass is wheat straw or pulping liquor.

10. The process of claim 9 where the biomass is wheat straw.

11. The process of claim 9 where the biomass is pulping liquor.

12. The process of claim 1 wherein the phenolic compounds are selected from the group consisting of phenols, poly-phenols and a combination thereof.

13. A process for the production of butanol comprising the steps of: (1) reacting biomass with an oxidizing agent to produce unoxidized aromatic and/or phenolic compounds and $C_{1-6}$ linear and branched, saturated and unsaturated carboxylic acids; (2) separating the unoxidized aromatic and/or phenolic compounds from the $C_{1-6}$ carboxylic acids; (3) anaerobically fermenting the $C_{1-6}$ carboxylic acids in the presence of an anaerobic bacterium in its solventogenesis phase to produce a solvent comprised of butanol and non-fermentable carboxylic acids.

14. The process of claim 13 further comprising the step of forming an ester by reacting the non-fermentable acids and butanol produced in step (3).

15. The process of claim 14 wherein the ester is formed in a reaction carried out in the presence of a lipase enzyme.

16. The process of claim 15 wherein the lipase enzyme is immobilized in a packed bed.

* * * * *